United States Patent [19]

Kipper et al.

[11] Patent Number: 5,656,752
[45] Date of Patent: Aug. 12, 1997

[54] PREPARATION OF NAPHTHALOCYANINES

[75] Inventors: Juergen Kipper, Karlsruhe; Bernhard Albert, Maxdorf, both of Germany

[73] Assignee: BASF Aktiengesellschaft, Ludwigshafen, Germany

[21] Appl. No.: 522,365

[22] PCT Filed: Mar. 18, 1994

[86] PCT No.: PCT/EP94/00863

§ 371 Date: Sep. 28, 1995

§ 102(e) Date: Sep. 28, 1995

[87] PCT Pub. No.: WO94/22960

PCT Pub. Date: Oct. 13, 1994

[30] Foreign Application Priority Data

Mar. 30, 1993 [DE] Germany ............... 43 10 371.5

[51] Int. Cl.[6] .................................................. C09B 47/04
[52] U.S. Cl. .................. 540/143; 540/122; 540/139; 540/142
[58] Field of Search .................. 540/122, 139, 540/142, 143

[56] References Cited

FOREIGN PATENT DOCUMENTS

| 0 553 614 A1 | 7/1993 | European Pat. Off. . |
| 2200650 | 1/1988 | United Kingdom . |

OTHER PUBLICATIONS

J. Org. Chem. 29 (1964) 3591.

Cook et al., J. Chem. Soc., Perkin I 1988 pp. 2453–2458.

Reynolds et al. J. Org. Chem., 1964 p. 3591.

*Primary Examiner*—Mukund J. Shah
*Assistant Examiner*—Pavanaram K. Sripada
*Attorney, Agent, or Firm*—Oblon, Spivak, McClelland, Maier & Neustadt, P.C.

[57] ABSTRACT

A process is described for preparing alkoxy-octasubstituted metal-free or metal-containing naphthalocyanines by etherification of 1,4-dihydroxy-2,3-dicyanonaphthalene and formation of the metal-free naphthalocyanine with or without subsequent metallization.

4 Claims, No Drawings

PREPARATION OF NAPHTHALOCYANINES

This application is a 317 of PCT/EP94/00863 Mar. 18, 1994.

The present invention relates to a novel process for preparing alkoxy-octasubstituted metal-free or metal-containing naphthalocyanines by etherification of 1,4-dihydroxy-2,3-dicyanonaphthalene and formation of the metal-free naphthalocyanine with or without subsequent metallization.

EP-A-433 220 describes the preparation of metal-free and metal-containing naphthalocyanines starting from 1,4-dihydroxy-2,3-dicyanonaphthalenes. Furthermore, GB-A-2 200 650 discloses the preparation of these naphthalocyanines starting from 1,4-dialkoxy-2,3-dicyanonaphthalenes. Finally, individual steps are described in J. Org. Chem. 29 (1964), 3591, and in J. Chem. Soc., Perkin Trans. I (1988), 2453. However, it has been found that the prior art methods give the naphthalocyanines only in unsatisfactory yield and purity.

It is an object of the present invention to provide a novel process for preparing naphthalocyanines, which can be carried out in a simple manner and by means of which the target products can be obtained in high yield and purity.

We have found that this object is achieved by a process for preparing naphthalocyanines of the formula I

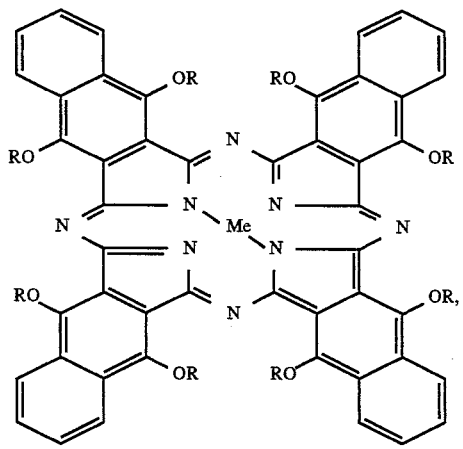

where

Me is twice hydrogen or a bivalent metal-containing radical with or without further ligands, and R is in each case $C_1$–$C_{20}$-alkyl, which may be interrupted by from 1 to 3 oxygen atoms in ether function, or $C_4$–$C_{20}$-alkenyl, by etherification of 1,4-dihydroxy-2,3-dicyanonaphthalene and formation of the metal-free naphthalocyanine with or without subsequent metallization, which comprises a) in a first step reacting the 1,4-dihydroxy-2,3-dicyanonaphthalene with an alkylating agent of the formula II

R—X (II), where X is bromine or the radical RO—SO$_2$O and R is in each case as defined above, in a molar ratio of from 1:2 to 1:3 in the presence of a diluent and of a base, pouring the reaction mixture onto water, filtering the precipitated dicyanonaphthalene of the formula III

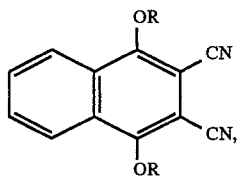

where R is in each case as defined above, off with suction, and washing and drying it, b) in a second step converting the dicyanonaphthalene of the formula III with an alkali metal alkoxide into the naphthalocyanine of the formula I where Me is twice hydrogen in the presence of an alcohol, the molar ratio of alkali metal alkoxide:dicyanonaphthalene, III being from 1:2.5 to 2.5:1, and optionally then c) in a third step converting the resulting metal-free naphthalocyanine by reaction with a metal salt in the presence of an alcohol into the metal-containing naphthalocyanine of the formula I where Me is a metal-containing ligand, the naphthalocyanine and the metal salt being reacted with each other in a molar ratio of from 1:1 to 1:10.

All alkyl and alkenyl groups appearing in the abovementioned formulae may be straight-chain or branched.

The radicals R can be identical or different.

R is for example methyl, ethyl, propyl, isopropyl, butyl, isobutyl, sec-butyl, pentyl, isopentyl, neopentyl, tert-pentyl, hexyl, 2-methylpentyl, heptyl, octyl, 2-ethylhexyl, isooctyl, nonyl, isononyl, decyl, isodecyl, undecyl, dodecyl, tridecyl, 3,5,5,7-tetramethylnonyl, isotridecyl (the above designations isooctyl, isononyl, isodecyl and isotridecyl are trivial names derived from the oxo process alcohols—cf. Ullmanns Encyklop adie der technischen Chemie, 4th Edition, Volume 7, pages 215 to 217, and also Volume 11, pages 435 and 436), tetradecyl, pentadecyl, hexadecyl, heptadecyl, octadecyl, nonadecyl, eicosyl, 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 2- or 4-butoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 4,8-dioxadecyl, 3,6,8-trioxadecyl, 3,6,9-trioxaundecyl, butenyl, but-3-en-1-yl, pentenyl, pent-4-en-1-yl, 3-methyl-but-3-en-1-yl, hexenyl, heptenyl, octenyl, nonenyl, decenyl, undecenyl, undec-10-en-1-yl, dodecenyl, tridecenyl, tetradecenyl, pentadecenyl, hexadecenyl, heptadecenyl, octadecenyl, nonadecenyl or eicosenyl.

A suitable bivalent metal-containing radical is in particular copper.

Preference is given to a procedure for preparing naphthalocyanines of the formula I where Me is twice hydrogen or copper.

Preference is further given to a procedure for preparing naphthalocyanines of the formula I where R is in each case $C_2$–$C_{13}$-alkyl or $C_4$–$C_{11}$-alkenyl or in particular $C_2$–$C_8$-alkyl, attention being drawn in particular to the preparation of those naphthalocyanines of the formula I where R is in each case $C_4$-alkyl or a $C_2/C_5$-alkyl mixture.

In Step 1 of the process of the invention, 1,4-dihydroxy-2,3-dicyanonaphthalene is reacted with an alkylating agent II in the presence of a diluent.

The molar ratio of 1,4-dihydroxy-2,3dicyanonaphthalene:alkylating agent II is from 1:2 to 1:3, preferably from 1:2.2 to 1:2.4.

As recited above, suitable alkylating agents are the corresponding bromine compounds (R—Br) or dialkyl sulfates (ROSO$_2$OR), the dialkyl sulfates being preferred in the case of lower alkyl (methyl or ethyl) while the bromine compounds are preferred for the other radicals.

The alkylating step is carried out in the presence of a diluent and of a base. Suitable diluents include for example N,N-dimethylformamide, N,N-diethylformamide, N-methylpyrrolidone and dimethyl sulfoxide. The use of N,N-dimethylformamide is preferred.

Suitable bases include for example alkali metal carbonates, such as lithium carbonate, sodium carbonate or potassium carbonate. The use of potassium carbonate is preferred.

The amount of base used is generally from 1.5 to 3 mol per mole of 1,4-dihydroxy-2,3-dicyanonaphthalene. The amount of diluent used is generally from 400 to 700% by weight, based on the weight of 1,4-dihydroxy-2,3-dicyanonaphthalene.

Step 1 of the process according to the invention is customarily carried out at from 80° to 120° C.

It is generally carried out by introducing the 1,4-dihydroxy-2,3-dicyanonaphthalene and the diluent as the initial charge and adding the base and the alkylating agent II. However, it is also possible to reverse this order and, for example, introduce the 1,4-dihydroxy-2,3-dicyanonaphthalene, the diluent and the alkylating agent II as the initial charge and add the base, or introduce the 1,4-dihydroxy-2,3-dicyanonaphthalene, the diluent and the base as the initial charge and add the alkylating agent II. The resulting mixture is then kept at the abovementioned temperature for from 4 to 10 hours with stirring.

In the rest of the workup, the mixture is poured onto water and the precipitated dicyanonaphthalene of the formula III is filtered off with suction, washed and dried.

Without further purification it can be used directly in Step 2 of the process according to the invention, which method is preferred.

The preparation of the starting 1,4-dihydroxy-2,3-dicyanonaphthalene is described for example in J. Org. Chem. 29 (1964), 3591.

In Step 2 of the process according to the invention, the dicyanonaphthalene of the formula III is converted into the metal-free naphthalocyanine of the formula I by means of an alkali metal alkoxide in the presence of an alcohol.

The dicyanonaphthalene III and the alkali metal alkoxide are used in a molar ratio of from 1:2.5 to 2.5:1, preferably from 1:2 to 2:1.

Suitable alkali metal alkoxides include for example lithium, sodium or potassium salts of methanol or ethanol. The use of the sodium or potassium salts is preferred, the use of sodium methoxide or sodium ethoxide being particularly preferred. It is further of particular advantage to add the alkali metal alkoxides in alcoholic solution.

Suitable alcohols include for example $C_1$–$C_{20}$-alkanols, whose alkyl chain may be interrupted by from 1 to 3 oxygen atoms in ether function, such as methanol, ethanol, propanol, isopropanol, butanol, isobutanol, sec-butanol, pentanol, isopentanol, neopentanol, tert-pentanol, hexanol, heptanol, octanol, isooctanol, 2-ethylhexanol, nonanol or decanol, or $C_4$–$C_{20}$-alkenols, such as but-3-en-1-ol, pent-4-en-1-ol or undec-10-en-1-ol.

The use of $C_2$–$C_{12}$-alkanols or $C_4$–$C_{11}$-alkenols is preferred, with $C_3$–$C_6$-alkanols being particularly preferred.

The alcohol is generally used in an amount of from 300 to 1000% by weight, based on the weight of dicyanonaphthalene of the formula III.

Step 2 of the process according to the invention is advantageously carried out by introducing the alkali metal alkoxide, the alcohol and the dicyanonaphthalene III as the initial charge and heating said initial charge with stirring to 90°–160° C. with or without a protective gas atmosphere, for example nitrogen or helium.

It is also possible to use as the initial charge a solution, for example of sodium methoxide in methanol, together with the alcohol and to heat this mixture to distill off methanol. After the methanol has been removed, the dicyanonaphthalene III can be added.

The reaction generally takes from 0.25 to 6 hours. The alcohol can then be distilled off in full or in part (at least half being removed), methanol added to the residue, and the precipitated metal-free naphthalocyanine of the formula I (Me=twice hydrogen) filtered off with suction, washed with methanol and dried.

The metal-free naphthalocyanine is obtained in good purity and can without further purification be used directly further, for example for the metallization reaction.

The resulting naphthalocyanine is found to have undergone a transalkylation (up to 100%) of the R radicals in that, during the formation of the naphthalocyanine, all or some of the OR radicals present on the naphthalene ring are replaced by the alkoxide radicals of the alcohol used.

It is also possible to transalkylate the ready-formed octaalkoxynaphthalocyanine. This can be done for example by treating the octaalkoxynaphthalocyanine with sodium methoxide and an alcohol whose alkoxy moiety is different from the alkoxy groups present on the naphthalocyanine.

The metal-free naphthalocyanine of the formula I is then optionally convertible in a third step into a metal-containing naphthalocyanine. For this it is reacted with a metal salt in the presence of an alcohol. The naphthalocyanine and the metal salt are used in a molar ratio of from 1:1 to 1:10, preferably from 1:1 to 1:1.2.

Step 3 can also be carried out by using the as-obtained reaction mixture of Step 2 directly, ie. without intermediate isolation of the metal-free naphthalocyanine. This method is preferred.

The alcohol is generally used in an amount of from 1000 to 2000% by weight, based on the weight of metal-free naphthalocyanine I.

Suitable metal salts include for example copper salts, such as copper(II) acetate, copper(I) chloride, copper(II) chloride, copper(II) sulfate and copper(II). acetylacetonate. The use of copper(II) acetate or copper(I) or copper(II) chloride is preferred.

Suitable alcohols for this step include for example propanol, butanol or pentanol.

When the metallization is carried out without intermediate isolation of the metal-free naphthalocyanine, an alcoholic reaction medium is already present. In this case the metallization can be carried out directly in this medium or, if necessary, the medium can be additionally diluted with further alcohol.

In some cases it can also be of advantage to carry out the metallization in the presence of bases, for example 1,4-diazabicyclo[2.2.21]octane or 1,5-diazabicyclo[5.4.0] undec-5-ene.

Step 3 of the process according to the invention is advantageously carried out by heating a mixture of metal-free naphthalocyanine I, metal salt and diluent with or without base to 80°–160° C. with stirring. The reaction generally takes from 5 to 20 hours. After the reaction has ended, the diluent can be distilled off in full or in part (at least half being removed). The residue can be admixed with petroleum ether and the metal-containing naphthalocyanine filtered off with suction, washed and dried.

The process of the invention, which can be carried out continuously as well as batchwise, is simple to practice and provides the target products in high yield and purity, the yield and purity of the novel process being distinctly higher than in the abovementioned, prior art processes.

The metal-free or metal-containing naphthalocyanines of the formula I are useful IR-absorbing compounds, which can be used for example in printing inks (see for example EP-A-0 553 614).

The Examples which follow illustrate the invention.

I. Alkylation

EXAMPLE 1

42 g (0.2 mol) of 1,4-dihydroxy-2,3-dicyanonaphthalene and 200 ml of N,N-dimethylformamide (DMF) were introduced at room temperature as the initial charge. 55.4 g (0.44 mol) of dimethyl sulfate and 60.8 g (0.44 mol) of potassium carbonate were added. The batch was slowly heated to 100° C. and stirred at that temperature for 8 h. It was then poured onto water, and the resulting precipitate was filtered off with suction, washed With water and dried to leave 30 g of 1,4-dimethoxy-2,3-dicyanonaphthalene (theory: 64%; melting point: 190° C.).

EXAMPLE 2

21 g (0.1 mol) of 1,4-dihydroxy-2,3-dicyanonaphthalene, 100 ml of dimethyl sulfoxide and 38.5 g (0.25 mol) of diethyl sulfate were introduced at room temperature as the initial charge. 38.6 g (0.28 mol) of potassium carbonate were added with stirring. The batch was then stirred at 100° C. for 10 h and thereafter poured onto ice-water, and the resulting precipitate was washed with water and dried to leave 23.3 g of 1,4-diethoxy-2,3-dicyanonaphthalene (theory: 87%; melting point: 167° C.).

EXAMPLE 3

210 g (1 mol) of 1,4-dihydroxy-2,3-dicyanonaphthalene, 1 l of DMF and 339 g (2.2 mol) of diethyl sulfate were introduced at room temperature as the initial charge. 304 g (2.2 mol) of potassium carbonate were added with care. The batch was gradually heated to 100° C. and stirred at 100° C. for 6 h. It was then poured onto water and the resulting precipitate was washed with water and dried to leave 231 g of 1,4-diethoxy-2,3-dicyanonaphthalene (theory: 87% ; melting point: 167°–169° C.).

EXAMPLE 4

105 g of 1,4-dihydroxy-2,3-dicyanonaphthalene, 145 g of potassium carbonate and 500 ml of DMF were introduced as the initial charge. 155 g of 4-bromobutane were added. The batch was then heated to 100° C. with stirring and subsequently stirred at that temperature for 6 hours. Thereafter the reaction mixture was cooled down and poured into 2000 ml of ice-water. The precipitate was filtered off with suction, washed with water and dried at 60° C. under reduced pressure to leave 120 g of 1,4-dibutoxy- 2,3-dicyanonaphthalene (theory: 90%; melting point: 69°–70° C.).

II. Naphthalocyanine formation

EXAMPLE 5

3 g (0.13 mol) of sodium were dissolved in 500 ml of ethanol, and 53.2 g (0.2 mol) of 1,4-diethoxy-2,3-dicyanonaphthalene were added. The batch was then stirred under reflux for 4 h. Almost all the ethanol (about 450 ml) was then distilled off under a water pump vacuum. Thereafter 600 ml of methanol were added to the reaction mixture and the reaction mixture was then stirred at room temperature for 5 h. The precipitated product was filtered off with suction, washed with methanol and dried to leave 23 g of octaethoxynaphthalocyanine (theory: 43%; $\lambda_{max}$: 856 nm; $\epsilon$: 264 000 (in toluene)).

EXAMPLE 6

47 g (0.26 mol) of 30% strength by weight methanolic sodium methoxide solution and 700 ml of n-propanol were introduced as the initial charge. The methanol was then distilled off under atmospheric pressure until just below the boiling point of propanol (97° C.). After cooling down, 106 g (0.4 mol) of 1,4-diethoxy-2,3-dicyanonaphthalene were added under nitrogen and the batch was subsequently stirred under reflux for 3 h. The propanol was then distilled off under a water pump vacuum except for about 50 ml, and 1 l of methanol was added. After stirring at room temperature for 8 h the precipitated product was filtered off with suction, washed with methanol and dried to leave 61.8 g of a naphthalocyanine which according to N-NMR had been 75% transalkoxylated (R=75% propyl and 25% ethyl) (theory: 53%, $\lambda_{max}$: 858 nm; $\epsilon$: 263 000 (in toluene)).

EXAMPLE 7

25 ml of 30% strength by weight methanolic sodium methoxide solution and 500 ml of butanol were introduced as the initial charge. The methanol was distilled off under atmospheric pressure to just below the boiling point of butanol. (117.8° C.). After cooling down, 65 g of 1,4-dibutoxy-2,3-dicyanonaphthalene were added under nitrogen and the batch was subsequently stirred under reflux for 2 h. Then 350 ml of butanol were distilled off and 400 ml of methanol were added. After stirring at room temperature for 12 h the precipitated product was filtered off with suction, washed with methanol and dried to leave 45 g of octabutoxynaphthalocyanine (theory: 70%).

EXAMPLE 8

47 g (0.26 mol) of 30% strength by weight methanolic sodium methoxide solution were added to 1 l of n-pentanol. Methanol was distilled off under atmospheric pressure to just below the boiling point of pentanol (about 137° C.). After cooling down, 106.4 g (0.4 mol) of 1,4-diethoxy-2,3-dicyanonaphthalene were added under nitrogen and the batch was stirred under reflux for 3 h. The pentanol was distilled down to a remainder of about 50 ml under a water pump vacuum, and 1 l of methanol was added. After stirring at room temperature for 10 h the precipitated product was filtered off with suction, washed with methanol and dried to leave 90.3 g of a partially transalkoxylated naphthalocyanine (R=88% pentyl and 12% ethyl) (theory: 66%; $\lambda_{max}$: 862 nm; 260 000 (in toluene)).

EXAMPLE 9

18 g (0.1 mol) of 30% strength by weight methanolic sodium methoxide solution and 300 ml of n-hexanol were introduced as the initial charge. Methanol was distilled off under atmospheric pressure to 153° C. After cooling down, 11.4 g (0.01 mol) of an octaalkoxynaphthalocyanine (R=70% propyl and 30% ethyl) were added and the batch was stirred under reflux for 4 h. Hexanol was distilled off almost to dryness under a water pump vacuum. Then 500 ml of methanol were added. After stirring at room temperature for 6 h the precipitated product was filtered off with suction, washed with methanol and dried to leave 9.4 g of octahexyloxynaphthalocyanine (theory: 62%; $\lambda_{max}$: 864 nm; $\epsilon$: 208 000 (in toluene)).

III. Metallization

EXAMPLE 10

45 g (0.035 mol) of octabutoxynaphthalocyanine were stirred for 10 h under reflux with 7 g (0.039 mol) of copper(II) acetate monohydrate in 650 ml of n-butanol. Butanol was distilled off under a water pump vacuum, the residue was stirred up with 700 ml of petroleumether for 1 h, filtered off with suction, washed with petroleum ether and dried to leave 42 g of copper octabutoxynaphthalocyanine (theory: 88%); $\lambda_{max}$: 849 nm; $\epsilon$: 235 000 (in toluene)).

IV. Naphthalocyanine formation and metallization in one pot

EXAMPLE 11

5.4 g (0.03 mol) of 30% strength by weight methanolic sodium methoxide solution and 180 ml of n-butanol were introduced as the initial charge at room temperature with stirring. Methanol was then distilled off under atmospheric pressure until the boiling point of n-butanol (117° C.) was reached in the reaction vessel. The solution was cooled down to 60° C. and admixed with 16.1 g (0.05 mol) of 1,4-dibutoxy-2,3-dicyanonaphthalene. The reaction mixture was then refluxed with stirring under nitrogen for 2 h, cooled down to 60° C. and admixed at that temperature with 1.9 g (0.0094 mol) of copper(II) acetate monohydrate. After 15 h of stirring under reflux, 80% of the total volume of n-butanol was distilled off under reduced pressure. The residue was stirred with petroleum ether (180 ml) at room temperature for 2 h, filtered off with suction and washed with petroleum ether to leave 13.4 g of copper octabutoxynaphthalocyanine (theory: 79.3% ; $\lambda_{max}$=850 nm; $\epsilon$=180 000 (in toluene)).

We claim:

1. A process for preparing naphthalocyanines of the formula I

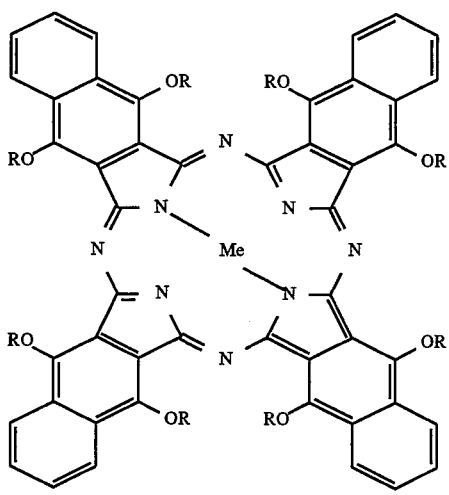

(I)

Me is twice hydrogen or a bivalent metal-containing radical with or without further ligands, and R is in each case $C_1$–$C_{20}$-alkyl, which may be interrupted by from 1 to 3 oxygen atoms in ether function, or $C_4$–$C_{20}$-alkenyl, by etherification of 1,4-dihydroxy-2,3-dicyanonaphthalene and formation of the metal-free naphthalocyanine with or without subsequent metallization, which comprises a) in a first step reacting the 1,4-dihydroxy-2,3-dicyanonaphthalene with an alkylating agent of the formula II

R—X  (II)

wherein X is bromine or the radical RO—$SO_2$O and R is in each case as defined above, in a molar ratio of from 1:2 to 1:3 in the presence of a diluent selected from the group consisting of N,N-dimethylformamide, N,N-diethylformamide, N-methylpyrrolidone and dimethylsulfoxide, and of a base, pouring the reaction mixture onto water, filtering the precipitated dicyanonaphthalene of the formula III

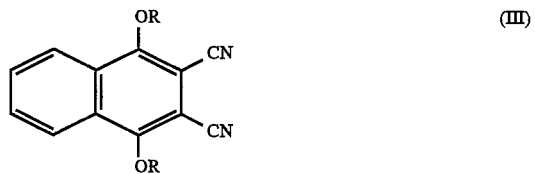

(III)

where R is in each case as defined above, off with suction, and washing and drying it, b) in a second step converting the dicyanonaphthalene of the formula III with an alkali metal alkoxide into the naphthalocyanine of the formula I where Me is twice hydrogen in the presence of an alcohol, the molar ratio of alkali metal alkoxide:dicyanonaphthalene III being from 1:2.5 to 2.5:1, and optionally then c) in a third step converting the resulting metal-free naphthalocyanine by reaction with a metal salt in the presence of an alcohol into the metal-containing naphthalocyanine of the formula I where Me is a metal-containing ligand, the naphthalocyanine and the metal salt being reacted with each other in a molar ratio of from 1:1 to 1:10.

2. A process as claimed in claim 1, wherein Me is twice hydrogen or copper.

3. A process as claimed in claim 1, wherein R is in each case $C_2$–$C_{13}$-alkyl or $C_4$–$C_{11}$-alkenyl.

4. A process as claimed in claim 1, wherein R is in each case $C_2$–$C_8$-alkyl.

* * * * *